United States Patent [19]

Kelman et al.

[11] Patent Number: 5,658,333
[45] Date of Patent: Aug. 19, 1997

[54] PROSTHESIS WITH HIGHLY CONVOLUTED SURFACE

[75] Inventors: David C. Kelman, Winona Lake; Todd S. Smith, Warsaw, both of Ind.

[73] Assignee: DePuy, Inc., Warsaw, Ind.

[21] Appl. No.: 647,146

[22] Filed: May 9, 1996

Related U.S. Application Data

[60] Continuation of Ser. No. 323,361, Oct. 14, 1994, abandoned, which is a division of Ser. No. 74,388, Jun. 10, 1993, Pat. No. 5,368,881.

[51] Int. Cl.$^6$ ............................................. A61F 2/28
[52] U.S. Cl. ............................. 623/16; 606/76; 427/2.26
[58] Field of Search ........................ 427/2.26, 2.27, 427/191; 606/76; 623/16, 22, 23

[56] References Cited

U.S. PATENT DOCUMENTS

| | | | |
|---|---|---|---|
| 2,356,513 | 8/1944 | Gonon | 427/2.27 |
| 4,168,326 | 9/1979 | Broemer et al. | 427/2.27 X |
| 4,542,539 | 9/1985 | Rowe et al. | 623/16 |
| 4,702,930 | 10/1987 | Heide et al. | 427/2.27 |
| 4,822,369 | 4/1989 | Oueveau et al. | 623/22 |
| 4,865,603 | 9/1989 | Noiles | 623/18 |
| 4,878,914 | 11/1989 | Miwa et al. | 623/16 |
| 5,263,986 | 11/1993 | Noiles et al. | 623/16 |
| 5,373,621 | 12/1994 | Ducheyne et al. | 29/527.2 |
| 5,405,389 | 4/1995 | Conta et al. | 623/16 |

FOREIGN PATENT DOCUMENTS

| | | | |
|---|---|---|---|
| 1148035 | 6/1983 | Canada | 427/191 |

*Primary Examiner*—David H. Willse
*Attorney, Agent, or Firm*—Perman & Green

[57] ABSTRACT

A technique for producing a highly convoluted surface on a prosthetic device is achieved by applying a layer of aspherical metallic powder on the surface of the device. The metallic powder, which may be the same as or different from the material of the device, is applied in a thickness of up to approximately 200 microns and has a size range of approximately −80 to +635 mesh so as to result in a desirable surface roughness defined by a peak to valley variation of up to approximately 200 microns. A resulting device has an enhanced surface which provides, alternatively, an improved press fit into a receiving bone, or improved cement fixation, or improved reception of a ceramic coating.

7 Claims, 2 Drawing Sheets

PROSTHESIS WITH HIGHLY CONVOLUTED SURFACE

This is a continuation of application Ser. No. 08/323,361, filed on Oct. 14, 1994, now abandoned, which is a divisional of application Ser. No. 08/074,388, filed on Jun. 10, 1993, now U.S. Pat. No. 5,368,881.

BACKGROUND OF THE INVENTION

1. Field of the Invention

The present invention relates to a technique for producing a highly convoluted surface on a prosthetic device.

Throughout the specification, the terms "aspherical" and "non-spherical" are used interchangeably and are intended to mean other than the spherical form.

2. Description of the Prior Art

There are a number of design criteria which have long been sought for the ideal segmental bone replacement implant. Three of these criteria are foremost: (1) the implant should last the lifetime of the patient without loss of function or initiating any adverse process response; (2) the implant should be designed to restore the normal function of the bone in which it is implanted; and (3) the implant must be producible on a commercial scale. To satisfy the foregoing criteria, it is necessary not only that the implant support the imposed load, often of a fluctuating nature, but also that the interface between the implant and the bone withstand the load requirement. This must be achieved on a regular and continuing basis.

A plastic cement such as polymethyl methacrylate is often used to affix the implant to the bone as well as to improve the fit between the implant and the bone. In another instance, prosthetic devices have been provided with porous coatings which fittingly mate with the bone and invite bone ingrowth such that, after a period of time, the prosthesis becomes integrated into the bone structure. Typical of such coatings are the disclosures in U.S. Pat., Nos. 3,855,638 and 4,206,516 to Pilliar, U.S. Pat. No. 4,156,943 to Collier, and U.S. Pat. No. 4,612,160 to Donlevy et al.

Ceramic coatings have also been used to good effect and are particularly desirable because of the affinity between the bone and ceramic materials such as alumina ($Al_2O_3$). Typical of the prior art in this regard are U.S. Pat. No. 4,145,764 to Suzuki et al and U.S. Pat. No. 4,483,678 to Nishio et al which are particularly concerned with dental implants and 4,309,488 to Heide et al and 4,846,837 to Kurze et al which more broadly disclose implantable bone replacement material for use throughout the body as appropriate.

It was in light of the prior art as just indicated that the present invention was conceived and has now been reduced to practice.

SUMMARY OF THE INVENTION

The present invention relates to a technique for producing a highly convoluted surface on a prosthetic device which is achieved by applying a coating of aspherical metallic powder on the surface of the device. The metallic powder, which may be the same as or different from the material of the device, is applied in a approximate thickness of up to approximately 200 microns and has a size range of approximately −80 to +635 mesh (178 microns to 35 microns) so as to result in a desirable surface roughness defined by a peak to valley variation up to approximately 200 microns $R_t$ as measured by laser profilometry. A resulting device has an enhanced surface which provides, alternatively, an improved press fit into a receiving bone, or improved cement fixation, or improved reception of a ceramic coating.

As originally conceived, the invention was intended to dramatically improve the interface bond strength of a ceramic coating to the prosthetic device itself. To this end, a highly convoluted surface is formed on the prosthetic device to which the ceramic coating can be applied, by whatever means. The highly convoluted surface can be produced, for example, by the sintering of a fine non-spherical powder on the surface of the implant. The fine powder yields a surface which is relatively non-porous but very highly convoluted. The convoluted surface provides greatly increased surface area for the chemical and mechanical interlock bonding of the ceramic to the implant substrate. The convoluted nature of the coating provides sites which protect the ceramic material from shear and tensile forces, thereby improving the bond strength.

Ceramic coatings are currently being applied to the surface of a prosthetic device in numerous ways which are cataloged, for example, in the patents noted above. Thus, application may be by way of sintering, hot-pressing, flame-spraying, plasma-spraying, sputtering, or other surface deposition techniques. The surface of the implant, in these instances, may or may not have any special treatments to enhance attachment of the coating. A typical surface treatment is to grit blast the surface of the device with an alumina abrasive to roughen the surface. The roughened surface provides an increase in surface area for improved bond strength as compared to a smooth surface and, to a certain extent, improves the shear strength of the interface bond between the ceramic and the implant. It is also known to apply the ceramic coatings to porous coatings intended for biological ingrowth for enhanced fixation.

The current method of grit blasting the surface, however, only slightly increases the roughness of the surface of the implant. Typically, the surface roughness after grit blasting is 50 microns $R_t$ which, offers only a minimal increase in surface area and mechanical interlocking of the ceramic to the implant. By way of contrast, the present invention provides a surface roughness up to approximately 200 microns $R_t$. Thus, the present invention goes beyond the point of a simple roughened surface to the point of utilizing a convoluted surface created specifically for ceramic attachment. As will be shown below, the convoluted surface of the invention yields far greater shear strength of the coating to the substrate as compared to conventionally roughened surface coatings.

Although, as noted above, the invention was originally conceived to improve the interface bond strength of a ceramic coating to the prosthetic device itself, it has been found to render superior results when applied to prosthetic devices utilizing different implanting techniques. Specifically, the resulting convoluted surface provided by the invention results in significantly greater friction between implant and bone when the implant is press fitted into the bone. Stronger bonding between cement and implant results also when cement is used for implant fixation.

Accordingly, it is an object of the invention to provide an improved technique for producing a highly convoluted surface on a prosthetic device.

It is a further object of the invention to apply a layer of aspherical metallic powder to the surface of a prosthetic device so as to yield a treated surface which is relatively non-porous and highly convoluted.

It is another object of the invention to apply to the surface of a prosthetic device a layer of aspherical metallic powder having a size range of approximately −80 to +635 mesh (178 microns to 35 microns) and in such a manner as to result in a surface roughness defined by a peak to valley variation of up to approximately 200 microns $R_t$.

Yet another object of the invention is to apply to the surface of a prosthetic device a layer of aspherical metallic powder composed of the same material as that of the surface.

Still another object of the invention is to apply to the surface of a prosthetic device a layer of aspherical metallic powder composed of a material different from that of the surface.

Yet a further object of the invention is to develop a surface of a prosthetic device which is formed from a powder coating of up to 200 microns in thickness and resulting in convolutions having a peak to valley variation of up to approximately 200 microns $R_t$.

Still a further object of the invention is to provide a prosthetic device with such a convoluted surface as recited above which results in significantly increased shear strength with bone cement.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

DETAILED DESCRIPTION OF THE PREFERRED EMBODIMENT

Figure 1:
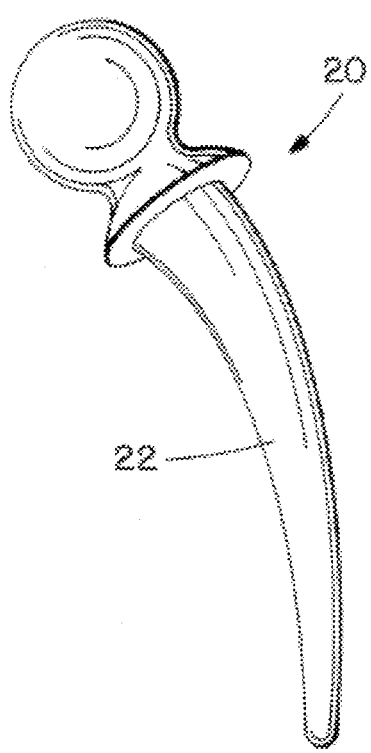
FIG. 1 is a perspective view of a femoral component for a hip prosthesis which has been modified in accordance with the present invention.
Figure 2A:
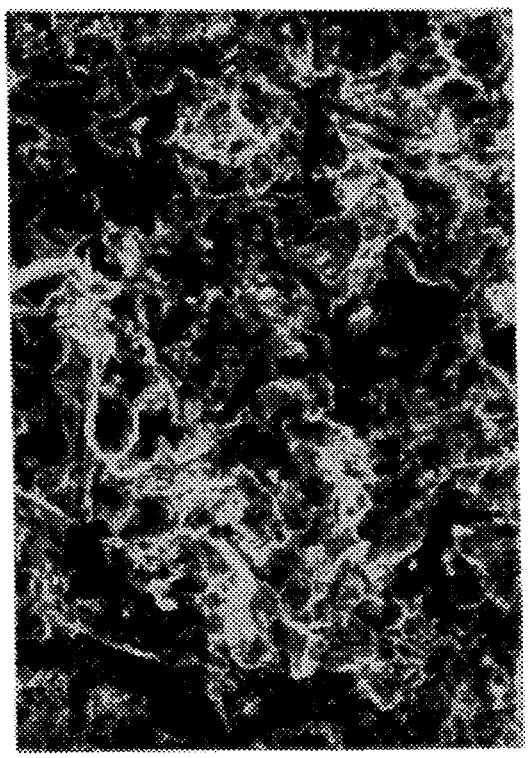
FIG. 2A is a scanning electron microscope (SEM) photomicrograph, magnification 100×, illustrating a typical surface of an implant which has been roughened by the conventional grit blast method.
Figure 3A:
FIGS. 3A and 3B are SEM photomicrographs, similar to FIGS. 2A and 2B, but with magnification 500×.
Figure 4A:
FIGS. 4A and 4B are SEM photomicrographs, similar to FIGS. 2A and 2B, with magnification 1000×.
Figure 2B:
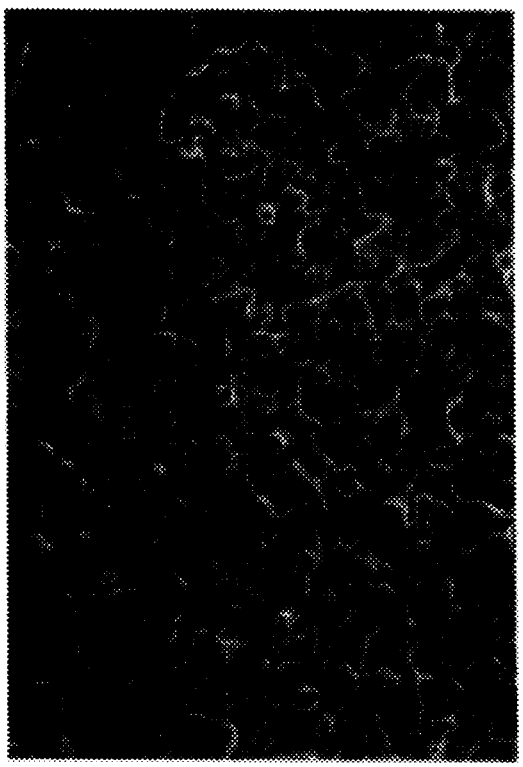
FIG. 2B is an SEM photomicrograph, magnification 100×, of the surface of an implant which has been modified in accordance with the invention.
Figure 3B:
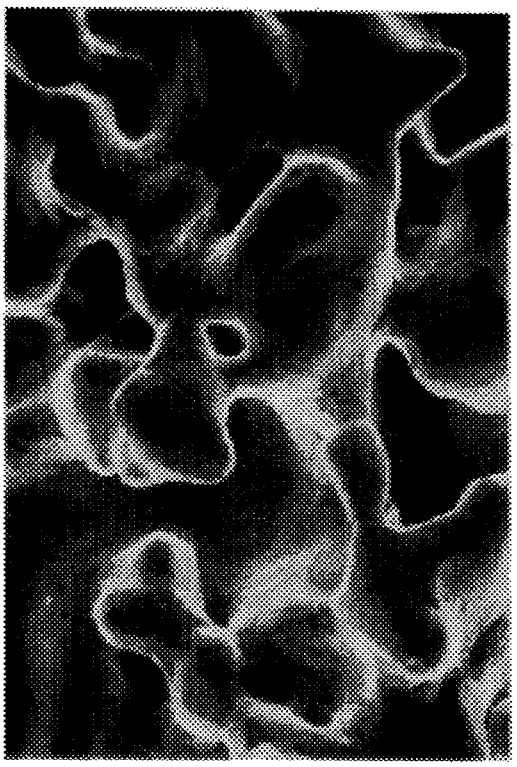
Figure 4B:
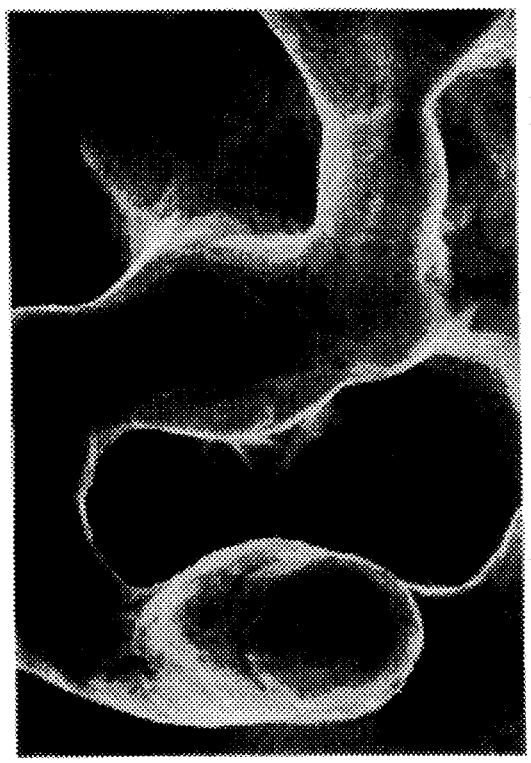

Turn now to the drawings and, initially, to FIG. 1 which illustrates a typical prosthetic implant 20 which has been modified in accordance with the invention. For purposes of explanation, the prosthetic implant 20 is a femoral component which includes a stem 22 intended for reception in the intramedullary cavity of a femur. Hence, the stem 22 is a mounting member for firmly attaching the implant to the bone. However, it will be appreciated that the invention is applicable to any prosthetic implant which is attachable to bone at any location within the body. The implant 20 may be composed of any of the biocompatible metals and alloys commonly used for prosthetic purposes, including titanium, cobalt chromium, and stainless steel.

The main thrust of the present invention is to produce a highly convoluted surface on the mounting member 22. This highly convoluted surface offers superior characteristics in resisting shear between the surface of the mounting member and any structure or coating which is intimate with that surface. In one such instance, the mounting member may be provided with a ceramic coating of the type commonly used in combination with a prosthetic implant. In another instance, the mounting member, in its roughened state, may be fittingly engaged with the bone as, for example, the stem 22 being fittingly received in the intramedullary canal of an associated femur. In still another instance, bone cement may be employed for fixing the mounting member to an underlying bone and, in that instance, improved bond strength between the mounting member and the cement, then with the bone, is achieved.

Ceramic coatings may be applied to the surface of a mounting member in a variety of ways including the plasma spray technique, sputtering, electro-phoresis and other surface deposition techniques. The surface of the implant may or may not have any special treatments to enhance attachment of the coating. A typical surface treatment is to grit blast the surface of the device with an alumina oxide abrasive to roughen the surface. The roughened surface provides an increase in surface area for improved bond strength as compared to a smooth surface, improving the shear strength of the interface bond between the ceramic and the implant. However, the current method of grit blasting the surface only slightly increases the surface roughness of the implant, typically, to about 50 microns $R_t$. The roughened surface thereby provided by grit blasting offers only a minimal increase in surface area and mechanical interlocking of the ceramic to the implant. In contrast, the present invention goes beyond the point of a simple roughened surface to the point of utilizing a highly convoluted surface which is vastly more tortuous than that produced by the grit blast method. The convoluted surface of the invention yields significantly greater shear strength of the coating to the substrate as compared to toughened surface coatings.

In order to achieve this desirable end result, a layer of non-spherical or aspherical material powder is suitably deposited onto the outer surface of the mounting member. The thickness of the coating may be up to approximately 200 microns. The implant is then subjected to a suitable heat treatment which may be by sintering according to any known process. The powder utilized for this purpose is of a biocompatible metal or metal alloy of the types normally employed for prosthetic implants, including titanium, cobalt chromium and stainless steel. However, the powder used need not be the same as its underlying substrate. Powders acceptable for purposes of the invention may be of a range of sizes between −80 mesh (178 microns to 35 microns) and +635 mesh, the larger the mesh size of the asymmetrical powder, the greater the surface roughness achieved. Optimum surface roughness achieved by the invention is a peak to valley variation of up to approximately 200 microns $R_t$. Powders suitable for purposes of the invention may be made using a variety of techniques including atomization, hydrogenization, and grinding, and are available from Cerac, Inc. of Milwaukee, Wis. under Product No. T-1146. In comparison, aspherical powders of both the −200 and −325 mesh size produce a more textured surface than any of the spherical powders of the same size.

While the practice of the invention results in a more textured surface, it also results in a substantially non-porous surface in contrast to highly porous coatings used on implants intended for bone ingrowth fixation such as the coating provided by DePuy Inc. under its proprietary POROCOAT trademark. It will be appreciated that a range of sizes of the powder utilized for coating the mounting member is a carefully defined range. If the powder is too fine in its texture, minor, ineffective, convolutions are obtained, while if the powder is too coarse in its texture, increased porosity occurs which is also unnecessary for purposes of the invention. The preferred range of powder sizes has been found to be approximately −80 mesh to +635 mesh (178 microns to 35 microns) in order to achieve the goals of the invention.

The following example is indicative of the mechanical performance achieved by the convoluted surface structure of the invention:

EXAMPLE

Titanium rods ⅝" in diameter were either polished to a typical polished implant finish, grit blasted with a 20 grit alumina oxide media (typical roughening process utilized), or a −200 or −325 mesh powder convoluted coating was applied. No ceramic material was applied to these specimens. What was being evaluated was the difference in shear strength provided by the different surface preparation techniques. A one inch length of the coated end of each bar was potted in Armstrong A-12 epoxy. The specimens were pulled apart in an Instron test machine. The resulting shear strengths of the various coating techniques are indicated in Table 1.

TABLE 1

| | SHEAR TEST RESULTS (PSI) | | |
|---|---|---|---|
| SATIN SMOOTH | 20 GRIT BLAST | −200 CON SUF | −325 CON SUF |
| 870 | 2290 | 2903 | 2955 |
| 1483 | 2004 | 2804 | 2920 |
| 1044 | 1915 | 2978 | 3419 |
| 770 | 2232 | 2746 | 3287 |
| 1656 | 1771 | 2222 | 2275 |
| AVG1165 | 2042 | 2731 | 2971 |

While a preferred embodiment of the invention has been disclosed in detail, it should be understood by those skilled in the art that various other modifications may be made to the illustrated embodiments without departing from the scope of the invention as described in the specification and defined in the appended claims.

What is claimed is:

1. A metallic substrate with a surface being of a biocompatible metal or alloy adapted for reception thereon of a ceramic coating comprising:

an intermediate coating on said surface of aspherical metallic powder in a size range of approximately 35 microns to 178 microns applied thereon up to a thickness of approximately 200 microns in such a manner that a resulting surface of said substrate after a heat treatment process is substantially non-porous and exhibits a surface roughness defined by a peak to valley variation up to approximately 200 microns.

2. A metallic substrate as set forth in claim 1 wherein said aspherical metallic powder is of the same metal or alloy as that of said surface.

3. A metallic substrate as set forth in claim 1 wherein said aspherical metallic powder is of a biocompatible metal or alloy different from said metal or alloy of said surface.

4. A metallic substrate as set forth in claim 1 including a prosthetic implant having a mounting member with said surface thereon.

5. A metallic prosthetic implant being of a biocompatible metal or alloy comprising a mounting member for implantation in a bone, to which said mounting member has been applied a coating on the surface thereof of aspherical metallic powder in a size range of approximately 35 microns to 178 microns up to a thickness of approximately 200 microns in such a manner that a resulting surface of said mounting member after a heat treatment process is substantially non-porous and exhibits a surface roughness defined by a peak to valley variation up to approximately 200 microns.

6. A metallic prosthetic implant as set forth in claim 5 wherein said aspherical metallic powder is of the same metal or alloy as that of said surface.

7. A metallic prosthetic implant as set forth in claim 5 wherein said aspherical metallic powder is of a biocompatible material different from said metal or alloy of said surface.

* * * * *